(12) United States Patent
Cittadini et al.

(10) Patent No.: US 10,285,930 B2
(45) Date of Patent: May 14, 2019

(54) COSMETIC AND THERAPEUTIC METHODS UTILIZING AN EXTRACT OF LYTHRUM SALICARIA

(71) Applicant: BASF Beauty Care Solutions France SAS, Lyons (FR)

(72) Inventors: Lysianne Cittadini, Miribel (FR); Louis Danoux, Saulxures-les-Nancy (FR); Nathalie Godard, Aveize (FR)

(73) Assignee: BASF Beauty Care Solutions France SAS, Lyons (FR)

( * ) Notice: Subject to any disclaimer, the term of this patent is extended or adjusted under 35 U.S.C. 154(b) by 0 days.

(21) Appl. No.: 15/539,203

(22) PCT Filed: Dec. 22, 2015

(86) PCT No.: PCT/FR2015/053700
§ 371 (c)(1),
(2) Date: Jun. 23, 2017

(87) PCT Pub. No.: WO2016/102874
PCT Pub. Date: Jun. 30, 2016

(65) Prior Publication Data
US 2017/0360692 A1    Dec. 21, 2017

(30) Foreign Application Priority Data
Dec. 23, 2014 (FR) ..................... 14 63205

(51) Int. Cl.
| | | |
|---|---|---|
| A61Q 19/06 | (2006.01) | |
| A61K 8/9789 | (2017.01) | |
| A61K 8/368 | (2006.01) | |
| A61Q 19/08 | (2006.01) | |
| A61K 8/97 | (2017.01) | |
| A61K 8/02 | (2006.01) | |
| A61K 8/34 | (2006.01) | |
| A61K 8/49 | (2006.01) | |
| A61K 8/73 | (2006.01) | |

(52) U.S. Cl.
CPC .......... *A61K 8/9789* (2017.08); *A61K 8/0216* (2013.01); *A61K 8/345* (2013.01); *A61K 8/368* (2013.01); *A61K 8/4973* (2013.01); *A61K 8/73* (2013.01); *A61K 8/97* (2013.01); *A61Q 19/06* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 7,419,688 B2 | 9/2008 | Perrier et al. | |
| 2010/0247434 A1* | 9/2010 | Greenway | A61K 31/192 424/1.69 |
| 2017/0112737 A1* | 4/2017 | Bernard | A61K 31/05 |

FOREIGN PATENT DOCUMENTS

| | | | |
|---|---|---|---|
| CN | 103861030 A | | 6/2014 |
| FR | 2835183 A1 | | 8/2003 |
| FR | 2883749 A1 | | 10/2006 |
| JP | 2003 002820 | * | 1/2003 |
| JP | 2003002820 A | | 1/2003 |
| KR | 100852737 B1 | | 8/2008 |
| KR | 20130060446 A | | 6/2013 |
| RO | 126901 A2 | * | 12/2011 |
| RO | 126901 A2 | | 12/2011 |
| WO | WO-2015/140470 A2 | | 9/2015 |

OTHER PUBLICATIONS

Piwowarski J. et al. Contribution of C-Glucosidic Ellagitannins to *Lythrum salicaria* L. Influence on Pro-Inflammatory Functions of Human Neutrophils. J of Natural Medicines 69(1)100-110, Sep. 25, 2014. (Year: 2014).*
Hwang E. et al. Gallic Acid Regulates Skin Photoaging in UVB Exposed Fibroblast and Hairless Mice. Phytotherapy Research 28: 1778-1788, Aug. 2014. (Year: 2014).*
Jouravel G. et al. New Biological Activities of *Lythrum salicaria* L . . . Cosmetics 4(52)1-16, 2017. (Year: 2017).*
Piwowarski J. et al. Anti-Hyalurinidase and Anti-Elastase Activity Screening of Tannin Rich Plant Materials . . . J of Ethnopharmacology 137(1)937-941, Sep. 1, 2011. (Year: 2011).*
Piwowarski J. et al. *Lythrum salicaria* L. Underestimated Medicinal Plant from European Traditional Medicine. J of Ethnopharmacology 170:226-250, Jul. 21, 2015. (Year: 2015).*
Tunalier Z. et al. Antioxidant, Anti-Inflammatory, Anti-Nociceptive Activities and Composition of *Lythrum salicaria* L. Extracts. J of Ethnopharmacology 110(3)539-547, Apr. 4, 2007. (Year: 2007).*
Dudonne St. et al. DNA Macroarray Study of Skin Aging Related Genes Expression Modulation by Antioxidant Plant Extracts . . . Phytotherapy Research 25(5)686-693, May 2011. (Year: 2011).*
Mr. Plantes, "Salicaire (*Lythrum salicaria*)", Retrieved from www.mr-plantes.com/2011/04/salicaire-lythrum-salicaria, Apr. 8, 2011.

(Continued)

*Primary Examiner* — Ralph J Gitomer
(74) *Attorney, Agent, or Firm* — Drinker Biddle & Reath LLP

(57) ABSTRACT

The present invention relates to the cosmetic and/or nutraceutical use of an extract of the *Lythrum salicaria* plant and/or of gallic acid and/or one of the gallic acid derivatives, in particular vescalagin and/or castalagin. Provided is a cosmetic care process comprising the application, preferably topically, of the *Lythrum salicaria* extract according to the invention and/or of gallic acid and/or of one of the gallic acid derivatives, in particular vescalagin and/or castalagin, more preferentially castalagin, or of a cosmetic composition comprising it, for maintaining and/or increasing collagen expression in the skin and/or the mucous membranes, for increasing the firmness of the skin and/or of the mucous membranes and/or maintaining and/or increasing lipolysis in skin adipocytes for inducing a slimming effect onto the skin and/or decreasing, preventing and/or treating the unaesthetic manifestations of cellulite, for example the orange peel appearance of the skin and/or the jodhpur thigh appearance.

21 Claims, No Drawings

(56) References Cited

OTHER PUBLICATIONS

Hwang, E., et al., "Gallic Acid Regulates Skin Photoaging in UVB-Exposed Fibroblast and Hairless Mice", Phytotherapy Research, 2014, vol. 28, No. 12, pp. 1778-1788.
Tunalier, Z., et al., "Antioxidant, Anti-Inflammatory, Anti-Nociceptive Activities and Composition of *Lythrum salicaria* L. Extracts", Journal of Ethnopharmacology, 2007, vol. 110, No. 3, pp. 539-547.
International Preliminary Report on Patentability for International Application No. PCT/FR2015/053700 dated Jun. 27, 2017 with English Translation Thereof Attached.
International Search Report for PCT/FR2015/053700 dated Jun. 10, 2016 with English Translation Thereof Attached.
Written Opinion of the International Searching Authority for PCT/FR2015/053700 dated Jun. 10, 2016 with English Translation Thereof Attached.

* cited by examiner

COSMETIC AND THERAPEUTIC METHODS UTILIZING AN EXTRACT OF LYTHRUM SALICARIA

RELATED APPLICATIONS

This application is a national stage application (under 35 U.S.C. § 371) of PCT/FR2015/053700, filed Dec. 22, 2015, which claims benefit of French Application No. 1463205, filed Dec. 23, 2014.

The present invention relates to the cosmetic or nutraceutical use of an extract of the *Lythrum salicaria* plant and/or of gallic acid and/or of one of the gallic acid derivatives, in particular vescalagin and/or castalagin, for maintaining and/or increasing collagen expression in the skin and/or the mucous membranes, in particular for maintaining and/or increasing the firmness thereof and/or for increasing lipolysis in skin adipocytes, in particular for inducing a slimming effect and/or for decreasing the unaesthetic appearances of cellulite, such as the orange peel appearance of the skin and/or the jodhpur thigh appearance. The present invention also relates to the dermatological use of such an extract and/or of gallic acid or of one of the gallic acid derivatives, in particular vescalagin and/or castalagin, for the treatment of pathological skin conditions involving a decrease in collagen expression and/or cellulite.

Collagen is a constitutive protein of the extracellular matrix present in vertebrate tissues, which is part of a protein family comprising 29 different types.

Among the various collagen types, type I collagen is found in many human tissues, such as tendons, ligaments, cornea and skin. Type I collagen is the predominant collagen in skin. It is part of the fibrillar collagens together with collagen III and V.

Fibrillar collagen is formed from a precursor, procollagen, which, after a step of maturation into tropocollagen, will assemble spontaneously into fibrils which will subsequently form fibres and, finally, bundles that can measure 1 to 10 µM in diameter. These bundles are stabilized by crosslinking.

It is the collagen which gives tissues their mechanical strength, thus playing a predominant part in maintaining their firmness.

Various physiological variations during a lifetime, such as a change in diet or successive diets, hormonal changes during puberty, pregnancy, or menopause, will lead to modifications of cutaneous tissues, inducing a loss of firmness and slackening of the tissues. This loss of firmness involves a decrease in the level of collagen. Several concomitant mechanisms are involved in the decrease in this level of collagen: a decrease in the proliferation of dermal fibroblasts, a decrease in collagen synthesis, and the degradation of collagen is increased by metalloproteinases, in particular collagenases, which are the enzymes responsible for collagen degradation. Thus, the collagen protein is a preferred target for research and innovations in the cosmetics and dermocosmetics field, but also the nutraceutical field, and there are many compositions on the market which aim to firm cutaneous tissues and to improve skin firmness.

There is thus a constant need to identify novel active ingredients capable of maintaining and/or increasing the firmness of tissues, in particular of the skin. In addition, there is a specific need in the cosmetics and dermatological field for the development of active ingredients that are slimming and/or that act on cellulite and/or that decrease the orange peel effect of the skin, in particular in women. Indeed, previous non-pathological physiological variations, such as a change in diet, hormonal variations, in particular during puberty, pregnancy or menopause, but also a poor diet, and a sedentary lifestyle, are all causes for weight gain and/or the appearance of cellulite, also called adiposis edematosa. Cellulite is associated with unaesthetic manifestations such as the appearance of a padded effect of the skin, termed "orange peel" effect located particularly on the thighs, the hips, the waist and the buttocks in women, and/or the jodhpur thigh appearance when the cellulite is located at the top of the thighs, on the buttocks and the hips, and/or water retention, generating a feeling of aesthetic discomfort.

The extracellular matrix (ECM), a support structure for tissues which contains collagen, is also present between the cells of the adipose connected tissue, which are the adipocytes.

Consequently, the identification of cosmetic ingredients which are both capable of acting on maintaining the functionality of the ECM in particular via collagen expression, but also capable of slimming and/or decreasing the unaesthetic effects of orange peel skin is of great cosmetic and dermatological interest. Moreover, this is precisely the problem to which the present invention applies.

Very surprisingly, the inventors have in fact discovered that an extract of the *Lythrum salicaria* plant, gallic acid and gallic acid derivatives, in particular vescalagin and castalagin, more preferentially castalagin, make it possible to maintain and/or increase collagen expression in the skin and/or the mucous membranes and thus to maintain and/or increase the firmness thereof. They have also discovered that said extract, gallic acid and gallic acid derivatives, in particular vescalagin and castalagin, also make it possible to increase lipolysis in skin adipocytes and therefore that they have a slimming effect onto the skin. The extract of the *Lythrum salicaria* plant according to the invention, gallic acid and gallic acid derivatives, in particular vescalagin and castalagin, by virtue of their properties, are thus most particularly suitable for decreasing, preventing and/or treating the unaesthetic manifestations of cellulite, for example the orange peel appearance and/or the jodhpur thigh appearance and/or water retention.

The invention has the advantage of providing a novel active ingredient that is active in maintaining and/or increasing collagen expression making it possible to maintain and/or increase the firmness of the tissues, in particular of human skin, making this active ingredient an ingredient that is particularly suitable as an active ingredient that is active on distended, slackened cutaneous tissues. The extract according to the invention, gallic acid and gallic acid derivatives, in particular vescalagin and castalagin, make it possible moreover to maintain and/or increase lipolysis in skin adipocytes, which make them a novel slimming ingredient that is particularly effective for decreasing, preventing and/or treating the unaesthetic manifestations of cellulite, for example the orange peel appearance and/or the jodhpur thigh appearance and/or water retention. Thus, the action of the extract according to the invention, of gallic acid and of gallic acid derivatives, in particular vescalagin and castalagin, is a dual action and thus of great cosmetic, dermatological and nutraceutical advantage. They also make it possible to decrease the number of ingredients in cosmetic, dermatological and nutraceutical compositions.

Another advantage of the present invention is that the extract according to the invention is an orally and/or topically acceptable, non-toxic natural plant extract, which can be easily formulated and which can be produced on an industrial scale under conditions that are fully compliant with sustainable development. In addition, gallic acid, and gallic acid derivatives, in particular vescalagin and castalagin, are susceptible of being obtained (advantageously are obtained) from such an extract (for example by purification).

The extract according to the invention is an extract of the *Lythrum salicaria* plant, commonly known as purple loosestrife or rainbow weed. It is a plant of the family Lythraceae that is very widespread in Europe, including in France, easily recognizable because of its pink to violet flowers in the form of spikes. It is a plant that is known for its anti-diarrhoea, tonic and haemostatic properties. Moreover, it has soothing and calmative properties and is active on certain skin ailments such as eczema and intertrigo.

Patent application KR100852737 describes an antioxidant effect and also an inhibitory effect on the development of hepatic fibrosis of a *Lythrum salicaria* root extract, while application CN103861030 describes a combination of several plants, including *Lythrum salicaria*, for the effect thereof in the treatment of psoriasis.

The *Lythrum salicaria* plant is also known in cosmetics as a skin-colouring agent in application FR2883749 filed by the applicant and in application FR2835183.

Moreover, application WO 2015/140470 describes the use of gallic acid and of gallic acid derivatives that can come from the *Lythrum salicaria* plant, as active ingredient in a cosmetic composition, for stimulating or repairing the barrier function of the epidermis, for combatting skin ageing, and for moisturizing it and combatting external attacks associated with pollution and with stress in dry skin that has a tendency to be atopic.

In addition, patent application JP2003002820 describes the cosmetic use of a *Lythrum salicaria* extract for its anti-elastase activity on the skin.

However, neither said application nor any prior art describes the properties of maintaining and/or increasing collagen protein expression, or of maintaining and/or increasing the firmness of the skin and/or of the mucous membranes. In addition, application KR20130060446 describes a therapeutic composition comprising a combination of a *Lythrum salicaria* extract and of an extract of the *Aceriphyllum rossii* plant for combatting obesity.

Furthermore, it is known that *Lythrum salicaria* is a tonic agent. However, for the purposes of the present invention, a distinction is made between a "tonic" agent which makes it possible to close the pores of the skin, and thus to tone the tissues by providing a non-lasting immediate effect of firmness, and the *Lythrum salicaria* extract according to the present invention which makes it possible to increase the firmness of the skin by increasing collagen expression. Finally, patent application RO126901 discloses the use of a *Lythrum salicaria* extract for the treatment of rosacea. Likewise, Tunalier et al. (2007) discloses the use of the *Lythrum salicaria* extract in the treatment of varicose veins.

No prior art describes, however, the use of a *Lythrum salicaria* extract and/or of gallic acid and/or of gallic acid derivatives, in particular vescalagin and/or castalagin, for increasing lipolysis in skin adipocytes in order to induce a slimming effect onto of the skin and/or to decrease the unaesthetic manifestations of cellulite, such as the orange peel appearance and/or the jodhpur thigh appearance. Moreover, no prior art describes the extract according to the invention for the dermatological use thereof for the treatment of cellulite.

Thus, a first subject of the present invention is the cosmetic use of an extract of the *Lythrum salicaria* plant for maintaining and/or increasing collagen expression in the skin and/or the mucous membranes. A subject of the present invention is thus also the cosmetic or nutraceutical use of an extract of the *Lythrum salicaria* plant for maintaining and/or increasing the firmness of the skin and/or of the mucous membranes, in particular in human beings. A subject of the present invention is also the cosmetic or nutraceutical use of an extract of the *Lythrum salicaria* plant for maintaining and/or increasing lipolysis in skin adipocytes and/or for inducing a slimming effect onto the skin and/or for decreasing, preventing and/or treating the unaesthetic manifestations of cellulite, for example the orange peel appearance of the skin.

The *Lythrum salicaria* extract according to the invention contains gallic acid and/or one of the gallic acid derivatives, in particular vescalagin and/or castalagin. A subject of the invention thus relates to the cosmetic and/or nutraceutical use of gallic acid and/or of one of the gallic acid derivatives, in particular of vescalagin and/or castalagin, preferentially castalagin, which is advantageously susceptible of being obtained, preferentially obtained, from the *Lythrum salicaria* plant, in particular by extraction from this plant, for maintaining and/or increasing collagen expression in the skin and/or the mucous membranes and also for maintaining and/or increasing the firmness of the skin and/or of the mucous membranes.

A subject of the present invention is also the cosmetic and/or nutraceutical use of gallic acid and/or of one of the gallic acid derivatives, in particular vescalagin and/or castalagin, which is advantageously susceptibleof being obtained, preferentially obtained, from the *Lythrum salicaria* plant, in particular by extraction from this plant, for maintaining and/or increasing lipolysis in skin adipocytes and/or for inducing a slimming effect onto the skin and/or for decreasing, preventing and/or treating the unaesthetic manifestations of cellulite, for example the orange peel appearance of the skin and/or the jodhpur thigh appearance.

For the purposes of the present invention, the term "cosmetic use" is intended to mean a non-therapeutic use, that is to say a use such that the *Lythrum salicaria* extract and/or the gallic acid and/or one of the gallic acid derivatives, in particular vescalagin and/or castalagin, more preferentially castalagin, is applied to all or part of the healthy body, particularly to a healthy area of skin and/or of mucous membrane.

For the purposes of the present invention, the term "healthy area of skin and/or of mucous membrane" is intended to mean an area of skin and/or of mucous membrane described as non-pathological by a dermatologist, that is to say an area which does not exhibit any skin infection, disease or ailment such as candidosis, impetigo, psoriasis, eczema, acne or dermatitis, or any wounds or injuries, or any disease associated with a dysfunction of lipolysis in adipose tissues, particularly in adipocytes, such as obesity, or any varicose veins, rosacea or telangiectasia.

In particular, the term "healthy area of skin and/or of mucous membrane" is intended to mean an area of skin and/or of mucous membrane consisting of cells described as "normal" by a physician, that is to say non-cancerous cells.

For the purpose of the present invention, the term "mucous membrane" is intended to mean the ocular mucous membrane, the vaginal mucous membrane, the urogenital mucous membrane and/or the buccal mucous membrane, in particular labial buccal mucous membrane and/or the gingival mucous membrane, preferentially the ocular and/or buccal mucous membranes, and more preferentially the labial and/or ocular mucous membrane.

For the purposes of the present invention, the term "skin" is intended to mean the skin of the face and/or of the body, including the scalp, and the term "scalp" is intended to mean the temporal areas of the scalp, the frontal area, the parietal area and the vertex or top of the head. It is advantageously the skin of the body.

Thus, advantageously, the *Lythrum salicaria* extract and/or gallic acid and/or one of the gallic acid derivatives, in particular vescalagin and/or castalagin, more preferentially castalagin, is applied, in particular by massaging with circular movements, to at least one area of skin and/or of mucous membrane chosen from the stomach, the arms, the forearms, the knees, the bust, the thighs, the hips, the buttocks, the neck, the waist and/or the face, and preferentially the body, in particular to an area of skin comprising cellulite and/or unaesthetic manifestations thereof, such as the orange peel appearance or the jodhpur thigh appearance, and/or to an area of skin which lacks firmness owing to non-pathological physiological variations such as a change in diet, hormonal variations, in particular during puberty, pregnancy or menopause, but also a poor diet, or a sedentary lifestyle, and more particularly in women.

More advantageously, the *Lythrum salicaria* extract and/or gallic acid and/or one of the gallic acid derivatives, in particular vescalagin and/or castalagin, more preferentially castalagin, is applied to an area of skin which is not dry and/or does not have a tendency to be atopic and/or the barrier function of the epidermis of which is not modified and/or the skin slackening of which is not due to an effect of extrinsic or intrinsic (chronobiological or photo induced) ageing.

The extract according to the invention and/or gallic acid and/or one of the gallic acid derivatives, in particular vescalagin and/or castalagin, more preferentially castalagin, can be administered orally in nutraceutical supplement form or in topical form. Preferentially, it is administered topically. Thus, the extract according to the invention and/or gallic acid and/or one of the gallic acid derivatives, in particular vescalagin and/or castalagin, more preferentially castalagin, is topically and/or orally acceptable. For the purposes of the present invention, the term "topically and/or orally acceptable" is intended to mean an extract and/or gallic acid and/or one of the gallic acid derivatives, in particular vescalagin and/or castalagin, more preferentially castalagin, which is non-toxic and non-irritant to the skin and/or the mucous membranes, does not induce an inflammatory response, particularly does not induce an allergic response and is chemically stable.

For the purposes of the present invention, the term "topical use" or "topically" is intended to mean the use of the extract according to the invention and/or of gallic acid and/or of one of the gallic acid derivatives, in particular vescalagin and/or castalagin, more preferentially castalagin, by direct local application, such as massaging with circular movements, and/or spraying of the ingredient onto the surface of the area of the skin and/or of the mucous membranes that is involved.

For the purposes of the present invention, the term "collagen" is intended to mean type I and/or III and/or IV and/or V and/or VI and/or VII and/or XII and/or XIII and/or XIV and/or XVI and/or XVII and/or XXIV and/or XXIX collagen, in particular present in the skin and/or the mucous membranes. It is preferentially type I and/or III and/or V collagen, in particular present in the skin and/or the mucous membranes, and more preferentially type I collagen, in particular present in the skin and/or the mucous membranes, in particular human collagen.

The gallic acid according to the invention has the following formula (molecular weight=170.12 g/mol; CAS number 149-91-7):

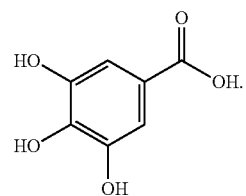 [SMILES: O=C(O)c1cc(O)c(O)c(O)c1]

For the purposes of the present invention, the term "gallic acid derivatives" is intended to mean the hydrolysable polymers of gallic acid, hexahydroxydiphenic acid, its polymers that are hydrolysable to hexahydroxydiphenic acid, ellagic acid, its polymers that are hydrolysable to ellagic acid, gallotanins and/or ellagitanins. Among the gallotanins, mention may be made of tannic acid and 1,2,3,4,6-penta-O-galloyl-beta-D-glucopyranose. Among the ellagitanins, mention may be made of vescalagin, castalagin, casuarinin, stachyurin, salicarinin A (vescalagin-stachyurin dimer), salicarinin B (vescalagin-casuarinin dimer) and salicarinin C (castalagin-casuarinin dimer). It is preferentially vescalagin and/or castalagin. Vescalagin has the following formula (molecular weight=934.07 g/mol; CAS number 36001-47-5):

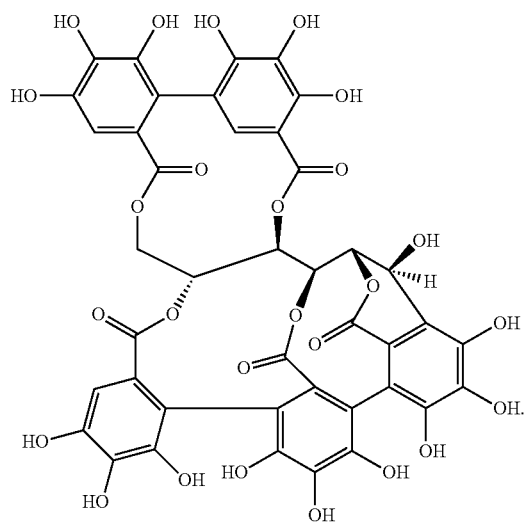 [SMILES: O=C1O[C@H]2[C@@H]3OC(=O)c4c(c(O)c(O)c(O)c4-c4c(O)c(O)c(O)c5c4C(=O)O[C@H]3[C@H]5O)-c3c(cc(O)c(O)c3O)C(=O)O[C@@H]2COC(=O)c2cc(O)c(O)c(O)c2-c2cc1c(O)c(O)c2O]

Castalagin has the following formula (molecular weight=934.63 g/mol; CAS number 24312-00-3):

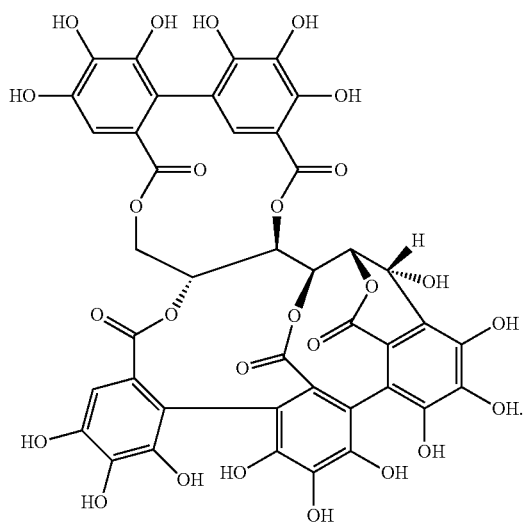 [SMILES: O=C1O[C@H]2[C@@H]3OC(=O)c4c(c(O)c(O)c(O)c4-c4c(O)c(O)c(O)c5c4C(=O)O[C@H]3[C@@H]5O)-c3c(cc(O)c(O)c3O)C(=O)O[C@@H]2COC(=O)c2cc(O)c(O)c(O)c2-c2cc1c(O)c(O)c2O]

Thus, a subject of the invention relates to the cosmetic use of gallic acid and/or of one of the gallic acid derivatives, in particular vescalagin and/or castalagin, more preferentially castalagin, which is more particularly susceptible of being obtained, preferentially is obtained, from the *Lythrum salicaria* extract according to the invention, for maintaining and/or increasing collagen expression in the skin and/or the mucous membranes, for maintaining and/or increasing the firmness of the skin and/or of the mucous membranes and also for maintaining and/or increasing lipolysis in skin adipocytes and/or for inducing a slimming effect onto the skin and/or for decreasing, preventing and/or treating the unaesthetic manifestations of cellulite, for example the orange peel appearance of the skin and/or the jodhpur thigh appearance.

In one preferential embodiment of the invention, the cosmetic use is the use of a *Lythrum salicaria* extract comprising gallic acid and/or one of the gallic acid derivatives, in particular vescalagin and/or castalagin, more preferentially castalagin, for maintaining and/or increasing collagen expression in the skin and/or the mucous membranes, for maintaining and/or increasing the firmness of the skin and/or of the mucous membranes and also for maintaining and/or increasing lipolysis in skin adipocytes and/or for inducing a slimming effect onto the skin and/or for decreasing, preventing and/or treating the unaesthetic manifestations of cellulite, for example the orange peel appearance of the skin and/or the jodhpur thigh appearance.

For the purposes of the present invention, the term "increasing collagen expression" is intended to mean increasing the gene expression, that is to say the expression of the mRNA, and/or the protein expression of collagen, preferentially increasing the protein expression of collagen, and more preferentially of type I collagen, in particular in the skin and/or the mucous membranes, advantageously of human type I collagen.

For the purpose of the present invention, the term "maintaining collagen expression" is intended to mean preventing collagen expression from decreasing. However, advantageously, for the purpose of the present invention, maintaining collagen expression is not preventing collagen degradation, in particular that induced by the action of metalloproteinases, in particular metalloproteinases 1 and 3 (MMP1 and MMP3).

In one embodiment of the invention, the extract and/or gallic acid and/or one of the gallic acid derivatives, in particular vescalagin and/or castalagin, more preferentially castalagin, is considered to be in an amount that is effective for increasing collagen gene and/or protein expression in fibroblasts cultured in vitro, when the gene and/or protein increase is at least 20%, preferentially at least 60%, more preferentially at least 80%, even more preferentially at least 90% relative to the level of collagen gene and/or protein expression measured in fibroblasts cultured in the absence of the extract, of the gallic acid and of the gallic acid derivatives, in particular of the vescalagin and of the castalagin, more preferentially the castalagin. In one preferential embodiment of the invention, the increase is the increase in type I collagen protein expression measured by the immunochemical technique in human fibroblasts cultured in the presence of the extract prepared according to example 1a), according to the protocol described in example 2.

In one alternative embodiment of the invention, the increase is the increase in type I collagen protein expression measured by the immunochemical technique in human fibroblasts cultured in the presence of the extract prepared according to example 1g).

Advantageously, the measurement by the immunochemical technique is carried out using an anticollagen I antibody, according to the protocol described in example 2.

Advantageously, for the purposes of the present invention, the human fibroblasts placed in culture are normal, that is to say non-pathological and non-cancerous, and consequently do not require any therapeutic treatment.

For the purposes of the present invention, the term "increasing the firmness" is intended to mean an increase for aesthetic purposes in the firmness of the skin and/or of the mucous membranes which have lost firmness, in particular under the effect of non-pathological physiological variations such as a change in diet, hormonal variations, in particular during puberty, pregnancy, menopause or andropause, a poor diet or a sedentary lifestyle, more advantageously which have lost firmness under the effect of non-pathological physiological variations such as a change in diet, hormonal variations, in particular during puberty, pregnancy, menopause or andropause, a poor diet or a sedentary lifestyle. This loss of firmness can also occur under the effect of extrinsic factors such as aggressive environmental agents, for example UV radiation, pollution, fumes, tobacco, toxins, climatic attacks and/or mechanical attacks.

For the purposes of the present invention, the term "maintaining the firmness" is intended to mean preventing slackening of the cutaneous tissues, of the skin and/or of the mucous membranes.

Advantageously according to the invention, the increase in the firmness of the skin and/or of the mucous membranes is not concomitant with an increase in the elasticity of the skin and/or of the mucous membranes. For the purposes of the present invention, a distinction is in fact made between the firmness of the skin, in particular closely linked to collagen synthesis, more particularly the synthesis of type I collagen, which is a protein that confers its mechanical strength of the extracellular matrix, and the elasticity of the skin, which is in particular dependent on the amount of functional elastic fibres.

The present invention thus excludes the use of the *Lythrum salicaria* extract and/or of gallic acid and/or one of the gallic acid derivatives, in particular vescalagin and/or castalagin, for maintaining and/or increasing the elasticity of the skin and/or of the mucous membranes, in particular inhibiting the activity of the elastases present in the skin and/or the mucous membranes. Moreover, the conventional methods for measuring the firmness of the skin consist in measuring the depth of its possible deformations, whereas those aimed at measuring the elasticity of the skin consist in measuring its capacity to return to its initial state after twisting and/or deformation.

The increase in the firmness can be measured according to the conventional methods, in particular by in vivo measurement by means of a cutometer, a density score, a torquemeter or else a dynaskin combined with a dermatop. The increase in the elasticity can be measured according to the conventional methods, in particular by in vivo measurement by means of a ballistometer or a corneovacumeter.

The extract according to the invention, gallic acid and gallic acid derivatives, in particular vescalagin and castalagin, more preferentially castalagin, are particularly advantageous for firming the body.

For the purposes of the present invention, the term "increasing lipolysis in skin adipocytes" is intended to mean an increase in the lipolytic activity measured in adipocytes cultured in vitro in the presence of the *Lythrum salicaria* extract according to the invention and/or of gallic acid and/or one of the gallic acid derivatives, in particular of vescalagin and/or of castalagin, preferentially castalagin, of at least 30%, preferentially of at least 35%, in particular of at least 40%, even more preferentially of at least 70%, relative to the lipolytic activity measured in the adipocytes cultured in vitro in the absence of the extract according to the invention, of gallic acid and of one of the gallic acid derivatives, in particular vescalagin and castalagin, more preferentially castalagin.

In one preferred embodiment, the increase in the lipolytic activity is measured in adipocytes obtained from a differentiation of normal, that is to say non-cancerous, preadipocytes, of a healthy human being, that is to say one showing no sign of obesity as defined by a physician, said adipocytes being cultured in vitro under the conditions described in example 3a). Advantageously, the lipolytic activity is measured by quantification of glycerol by measuring the optical density at 340 nm according to example 3a).

In one alternative embodiment, the increase in the lipolytic activity is measured in adipocytes obtained from a differentiation of normal, that is to say non-cancerous, murine preadipocytes, cultured in vitro under the conditions described in example 3b) in the presence of the *Lythrum salicaria* extract comprising vescalagin and castalagin, prepared according to example 1g).

For the purposes of the present invention, the term "maintaining lipolysis in skin adipocytes" is intended to mean preventing a decrease in lipolysis in skin adipocytes.

For the purposes of the present invention, the term "inducing a slimming effect onto the skin" is intended to mean a visually observable, and in particular quantifiable, decrease in the volume of the figure, preferentially in the waist size and/or in the hip size and/or in the size of the thighs and/or in the buttock volume. For the purposes of the present invention, it is not intended to mean a weight loss, but a remodelling of the figure.

The term "decreasing the unaesthetic manifestations of cellulite, for example the orange peel appearance and/or the jodhpur thigh appearance" is intended to mean a visual and measurable decrease in the unaesthetic manifestations of cellulite, for example by imaging, such as fringe projection at the surface of the skin (this measurement is preferentially carried out at the level of the hips and/or the buttocks and/or the stomach and/or the thighs, more preferentially in women), and/or a visually observable and quantifiable decrease in the orange peel appearance of the skin, that is to say a decrease in the visible nodes of fat and/or superficial fatty lumps of the body, in particular in the long term while preventing the reappearance thereof, and a smoother, more uniform appearance of the surface of the skin, preferentially at the level of the thighs (in particular the top of the thighs) and/or the hips and/or the stomach and/or the buttocks. For the purposes of the present invention, the term "orange peel appearance" is intended to mean a non-smooth, padded appearance of the skin which manifests itself through the presence of crevices and nodes of fat due to a deformation of the subcutaneous tissues of the skin, particularly of the hypodermis, owing in particular to an increase in the size of the adipocytes.

The term <<preventing the unaesthetic manifestations of cellulite, for example the orange peel appearance and/or the jodhpur thigh appearance" is intended to mean preventing the appearance of said manifestations.

The term "treating the unaesthetic manifestations of cellulite, for example the orange peel appearance and/or the jodhpur thigh appearance", is intended to mean causing said manifestations to disappear.

Thus, for the purposes of the present invention, the use of the *Lythrum salicaria* extract and/or of gallic acid and/or one of the gallic acid derivatives, in particular vescalagin and/or castalagin, for maintaining and/or increasing lipolysis in skin adipocytes, for inducing a slimming effect onto the skin and/or for decreasing, preventing and/or treating the unaesthetic manifestations of cellulite, for example the orange peel appearance of the skin and/or the jodhpur thigh appearance, is a non-therapeutic cosmetic use which is not intended for the treatment of obesity or for the treatment of a pathological skin condition.

The extract according to the invention can be an extract of all or part of the plant chosen from the whole plant, the aerial parts, the root, the seeds, the flowers, the petals, the sepals, the leafstalks, the flower peduncles, the flowering heads, the leaves, the fruit, the stem and/or any combination thereof. Preferentially, the extract according to the invention is an extract of the aerial parts of the plant. For the purposes of the present invention, the term "aerial parts" is intended to mean a mixture of leaves, flowers, flower peduncles and the stem.

The *Lythrum salicaria* extract according to the invention is obtained by any conventional plant extraction process known to those skilled in the art. The whole plant or the part of the plant concerned is thus dried and/or milled before extraction. The extraction can be carried out by maceration, by hot decoction, by milling using a ball mill, milling with a mortar or with ultrasound, by milling using a mixer or else by extraction under subcritical or supercritical conditions (carbon dioxide). Preferentially, the extraction is carried out by maceration.

In one preferential embodiment of the invention, the *Lythrum salicaria* extract is obtained by maceration of at least one part of the plant, preferentially the aerial parts, in a solvent or a mixture of solvents, preferably a protic polar solvent, and advantageously in water, an alcohol, a glycol, a polyol, a water/alcohol, water/glycol or water/polyol mixture (such as water as a mixture with ethanol, glycerol and/or butylene glycol and/or other glycols, such as xylitol, etc.) in any proportions, in particular from 100/0 to 0/100 (w/w). More preferentially, the solvent used is made up of water only. Even more preferentially the solvent used is a water/alcohol mixture, in particular water/ethanol, from 15/85 to 85/15 (w/w), in particular from 25/75 to 75/25 (w/w), more particularly from 60/40 to 85/15 (w/w), in particular of 75/25 (w/w).

In particular, the extract is obtained by aqueous extraction. For the purposes of the present invention, the term "extract obtained by aqueous extraction" is intended to mean any extract obtained by extraction with an aqueous solution containing more than 60% by weight, advantageously at least 70% by weight, in particular at least 80% by weight, more particularly at least 90% by weight, particularly at least 95% by weight, of water relative to the total weight of the aqueous solution, even more advantageously not containing glycol and particularly not containing alcohol, more particularly containing only water. Even more preferentially, the extract according to the invention is a *Lythrum salicaria* extract obtained by extraction with an aqueous solution containing ethanol, preferentially in an amount of from 15% to 40% by weight (w/w), more preferentially of 25% by weight (w/w) relative to the total weight of the aqueous solution.

The extraction can be carried out for a period ranging from 1 hour to 24 hours, in particular from 1 hour to 20 hours, preferentially from 2 hours to 24 hours, in particular from 2 hours to 16 hours. More preferentially, the extraction is carried out for a period of 2 hours. In one particularly advantageous embodiment of the invention, the extraction is carried out for a period of 24 hours.

The extraction can be carried out at a temperature of between 0° C. and 85° C., preferentially between 0° C. and 25° C., more preferentially between 4° C. and 20° C. Even more preferentially, the extraction is carried out at ambient temperature, that is to say at 20° C.

The extract can be obtained by extraction of an amount of from 0.1% to 10% by weight of dry matter of at least one part of the *Lythrum salicaria* plant relative to the total weight of the solvent/plant mixture (w/w). Preferentially, the extract is obtained by extraction of an amount of from 1% to 10% by weight, in particular from 1% to 5% by weight, and more advantageously of 5% or 10% by weight of dry matter of at least one part of the plant, relative to the total weight of the mixture consisting of the solvent, preferentially water, and of the plant (w/w).

In one preferential embodiment of the invention, the extract is obtained by maceration for a period of 2 hours at ambient temperature, that is to say 20° C., in water as sole solvent, of 5% by weight of the aerial parts, that is to say of the mixture of leaves, flowers, their peduncles and the stem, of the *Lythrum salicaria* plant, relative to the total weight of the water and of the aerial parts, as described in example 1a).

In another embodiment of the invention, the extract is obtained by maceration for a period of 1 hour at a temperature of 80° C., in water as sole solvent, of 5% by weight of the aerial parts, that is to say of the mixture of leaves, flowers, their peduncles and the stem, of the *Lythrum salicaria* plant, relative to the total weight of the water and of the aerial parts, as described in example 1 b).

In yet another embodiment of the invention, the extract is obtained by maceration for a period of 16 hours at a temperature of 4° C., in water as sole solvent, of 5% by weight of the aerial parts, that is to say of the mixture of leaves, flowers, their peduncles and the stem, of the *Lythrum salicaria* plant, relative to the total weight of the water and of the aerial parts, as described in example 1c).

In yet another embodiment of the invention, the extract is obtained by maceration for a period of 16 hours at a temperature of 4° C., in water as sole solvent, of 1% by weight of the aerial parts, that is to say of the mixture of leaves, stem and flowers, of the *Lythrum salicaria* plant, relative to the total weight of the water and of the aerial parts, as described in example 1d).

In an alternative embodiment of the invention, the extract is obtained by maceration for a period of 1 hour at a temperature of 80° C., in water as sole solvent, of 5% by weight of the leaves of the *Lythrum salicaria* plant, relative to the total weight of the water and of the leaves, as described in example 1e).

In yet another embodiment of the invention, the extract according to the invention is obtained by maceration in a water/ethanol mixture (75/25 w/w), for a period of 24 hours, of an amount of 10% by weight of the aerial parts, that is to say of the mixture of leaves, flowers, their peduncles and the stem, relative to the total weight of the mixture of solvent and of the aerial parts of the plant, under the conditions described according to example 1 g).

The crude extract obtained and used according to the invention is preferably then centrifuged and/or filtered and/or distilled in order to recover the soluble fraction, preferentially the water-soluble fraction. Preferentially, the supernatant obtained is then filtered, advantageously at a cut-off threshold of 0.45 µm. Additional decolouring and/or deodorizing steps can be carried out on the extract at any stage of the extraction and according to the techniques known to the one skilled in the art.

The extract can then be purified, by various purification methods known to those skilled in the art, for example by chromatography. Preferentially, the extract according to the invention is purified in a first step by solid phase extraction (SPE), in particular on a C18-grafted silica solid phase. The extract is deposited in an aqueous-alcoholic solution containing for example 20% of methanol and 0.5% of formic acid. The elution is carried out with this same solvent. The extract obtained can then be concentrated by evaporation and then lyophilized. The extract obtained can then be purified, for example in a second step, by semi-preparative high performance liquid chromatography (HPLC), preferentially on a Synergi Fusion (Phenomenex) column having the dimensions 250×10 mm. The elution is carried out for example with a gradient of 0.5% formic acid and methanol.

The purified *Lythrum salicaria* extract according to the invention, in particular obtained in this way, comprises vescalagin and/or castalagin, in a total amount of molecules of at least 0.25%, preferentially of at least 0.5%, more preferentially of at least 1% by weight relative to the total weight of the purified extract.

An additional step of adding maltodextrin can be carried out, for example after the purification of the extract. Advantageously, an amount of at least 20% by weight relative to the total weight of the extract and of the maltodextrin, preferentially of at least 50%, more preferentially of at least 70% by weight of maltodextrin, is then added to the extract. The extract can then be concentrated by evaporation of the solvent or dried for example by lyophilization or by spray-drying. Preferentially, the extract is dried by spray-drying.

In one preferential embodiment of the invention, the extract is dried by spray-drying after addition of maltodextrin to the solution. Advantageously, the amount by weight of maltodextrin added to the extract before the spray-drying step is such that the extract comprises 1% by weight of vescalagin and/or castalagin relative to the total weight of the powder thus obtained.

In one particular embodiment of the invention, in particular for use thereof in dermatology, the *Lythrum salicaria* extract obtained is sterilized.

According to the invention, the *Lythrum salicaria* extract and/or gallic acid and/or one of the gallic acid derivatives, in particular vescalagin and/or castalagin, can be used alone in the form of active ingredient and/or in a nutraceutical composition intended for oral application and/or in a cosmetic and/or dermatological composition intended for topical application, preferentially to the skin and/or the mucous membranes.

When it is used alone in the form of active ingredient, the extract and/or gallic acid and/or one of the gallic acid derivatives, in particular vescalagin and/or castalagin, more preferentially castalagin, is preferentially soluble and/or diluted in a solvent, in particular a polar solvent, such as water, an alcohol, a polyol, a glycol, such as pentylene glycol and/or butylene glycol and/or hexylene glycol and/or caprylyl glycol, or a mixture thereof, preferentially an aqueous-glycolic mixture, more preferentially containing a glycol chosen from hexylene glycol, caprylyl glycol and mixtures thereof.

Advantageously, the extract obtained and/or the gallic acid and/or one of the gallic acid derivatives, in particular vescalagin and/or castalagin, more preferentially castalagin, is diluted and/or soluble in an aqueous solution containing hexylene glycol, in particular containing between 0.1% and 10% by weight of hexylene glycol, preferentially between 0.5% and 5% by weight of hexylene glycol, relative to the total weight of the aqueous solution.

Advantageously, the extract obtained and/or the gallic acid and/or one of the gallic acid derivatives, in particular vescalagin and/or castalagin, more preferentially castalagin, is diluted and/or soluble in an aqueous solution containing caprylyl glycol, in particular containing between 0.01% and 5% by weight of caprylyl glycol, preferentially between 0.1% and 1% by weight of caprylyl glycol, relative to the total weight of the aqueous solution.

In particular, the aqueous solution in which the *Lythrum salicaria* extract according to the invention and/or gallic acid and/or one of the gallic acid derivatives, in particular vescalagin and/or castalagin, more preferentially castalagin, is solubilized comprises xanthan gum, in particular between 0.01% and 5% by weight of xanthan gum relative to the total weight of the aqueous solution, more particularly between 0.1% and 1% by weight of xanthan gum relative to the total weight of the aqueous solution.

Particularly advantageously, the solution in which the *Lythrum salicaria* extract according to the invention and/or gallic acid and/or one of the gallic acid derivatives, in particular vescalagin and/or castalagin, more preferentially castalagin, is solubilized comprises hexylene glycol, caprylyl glycol and xanthan gum, in particular in the proportions indicated in example 4.

The *Lythrum salicaria* extract and/or gallic acid and/or one of the gallic acid derivatives, in particular vescalagin and/or castalagin, more preferentially castalagin, can also be used in a cosmetic and/or nutraceutical and/or dermatological composition. Thus, the composition comprises at least one cosmetically and/or dermatologically acceptable excipient.

The terms "cosmetically and/or dermatologically acceptable excipient" used herein mean that the composition or the components thereof are suitable for use in contact with human skin without undue toxicity, incompatibility, instability or allergic response, or equivalents thereto.

In one embodiment of the invention, the *Lythrum salicaria* extract is present in the cosmetic and/or nutraceutical and/or dermatological composition at a concentration of from $1\times10^{-4}\%$ to 10%, preferentially from $1\times10^{-4}\%$ to 5%, and more preferentially from $1\times10^{-3}\%$ to 3% by weight, relative to the total weight of the composition.

The cosmetic and/or nutraceutical composition can thus comprise gallic acid and/or one of the gallic acid derivatives, in particular vescalagin and/or castalagin, more preferentially castalagin, at a total final concentration of molecules of from $2.5\times10^{-7}$ to 0.1%, preferentially from $5\times10^{-7}$ to 0.05%, more preferentially from $1\times10^{-5}\%$ to 0.03% by weight, relative to the total weight of the composition.

Advantageously, said excipient(s) are chosen from at least one of the groups made up of preservatives, emollients, emulsifiers, surfactants, moisturizers, thickeners, texturing agents, film-forming agents, pigments, stabilizers, solubilizers, dyes and fragrances.

Likewise advantageously, the excipient(s) are chosen from the group consisting of amino acids and derivatives thereof, polyglycerols, esters, polymers and derivatives of cellulose, lanolin derivatives, phospholipids, lactoferrins, lactoperoxidases, sugar-based stabilizers, vitamin E and derivatives thereof, xanthan gums, natural and synthetic waxes, vegetable oils, triglycerides, unsaponifiable compounds, phytosterols, plant esters, silicones and silicone derivatives, protein hydrolysates, jojoba oil and derivatives thereof, liposoluble/water-soluble esters, betains, amine oxides, plant extracts, saccharose esters, titanium dioxides, glycines, and parabens, and more preferably from the group consisting of steareth-2, steareth-21, glycol-15 stearyl ether, cetearyl alcohol, phenoxyethanol, methylparaben, ethylparaben, propylparaben, butylparaben, butylene glycol, caprylyl glycol, natural tocopherols, glycerin, dihydroxycetyl sodium phosphate, isopropyl hydroxycetyl ether, glycol stearate, triisononanoin, octyl cocoate, polyacrylamide, isoparaffin, laureth-7, a carbomer, propylene glycol, hexylene glycol, glycerol, bisabolol, a dimethicone, sodium hydroxide, PEG-dipolyhydroxystearate, capric/caprylic triglycerides, cetearyl octanoate, dibutyl adipate, grapeseed oil, jojoba oil, magnesium sulfate, EDTA, a cyclomethicone, xanthan gum, citric acid, sodium lauryl sulfate, mineral waxes and oils, isostearyl isostearate, propylene glycol dipelargonate, propylene glycol isostearate, PEG 8, beeswax, hydrogenated palm kernel oil glycerides, lanolin oil, sesame oil, cetyl lactate, lanolin alcohol, castor oil, titanium dioxide, lactose, saccharose, low-density polyethylene, and an isotonic saline solution.

The cosmetic and/or dermatological composition of the invention can be chosen from an aqueous or oily solution, a cream or a gel which is aqueous or an oily gel, in particular a shower gel, a shampoo, a milk, a body milk, an emulsion, a microemulsion or a nanoemulsion, which is in particular oil-in-water or water-in-oil or multiple or silicone-based, a mask, a serum, a lotion, a liquid soap, a dermatological bar, an ointment, a foam and a patch.

Preferentially, the cosmetic composition according to the invention is a cream or a serum. In one alternative embodiment of the invention, the composition is a body milk.

Advantageously, the cosmetic and/or dermatological composition is intended to be applied to at least one area of skin and/or of mucous membrane chosen from the stomach, the arms, the forearms, the knees, the bust, the thighs, the hips, the buttocks, the neck, the waist and/or the face, and preferentially the body, in particular to an area of skin comprising cellulite and/or the unaesthetic manifestations thereof, such as the orange peel appearance or the jodhpur thigh appearance, and/or to an area of skin which lacks firmness owing to non-pathological physiological variations such as a change in diet, hormonal variations, in particular during puberty, pregnancy or menopause, but also a poor diet, or a sedentary lifestyle, and more particularly in women.

In one alternative embodiment of the invention, the cosmetic and/or dermatological composition is applied, in particular by massaging with circular movements, to specific parts of the body chosen from the stomach, the arms, the thighs, the hips, the buttocks and/or the waist, preferentially the thighs and the hips.

In yet another embodiment of the invention, the composition is a nutraceutical composition that can be administered orally. Preferentially, said composition is in the form of gel capsules, a capsule, an oral powder, a gel and/or an oral liquid.

In addition, the cosmetic and/or nutraceutical composition of the present invention can contain one or more other cosmetic and/or nutraceutical active ingredients, resulting in a supplementary effect and/or a synergistic effect with the *Lythrum salicaria* extract according to the invention and/or gallic acid and/or one of the gallic acid derivatives, in particular vescalagin and/or castalagin, more preferentially castalagin.

They may for example be tensioning agents for a synergistic effect with the extract according to the invention. Advantageously, they are active ingredients which increase collagen gene and/or protein expression and/or prevent the degradation of said collagen, such as retinal, vitamin C, a *Quassia amara* extract or a *Davila rugosa* extract sold under the name Collguard™ by BASF Beauty Care Solutions, or active agents which stimulate the synthesis of the macromolecules of the dermis or prevent degradation thereof, such as:

an agent for protecting extracellular matrix fibroblast growth factor (FGF2) against degradation thereof and/ or denaturation thereof, in particular a *Hibiscus abelmoscus* extract as described in the patent application in the name of the applicant filed under number FR0654316;

an agent for stimulating fibroblast growth, for example a fermented soya extract containing peptides, known as Phytokine™ sold by the applicant and also described in patent application EP 1 119 344;

and/or also an agent for stimulating fibronectin synthesis, in particular a maize extract, such an extract being in particular sold by the applicant under the name Deliner™ or the products sold under the names Matrixyl™ (palmitoyl pentapeptide), Matrixyl 3000™ and Regestril™ by the company Sederma;

an agent for stimulating laminin synthesis, in particular a biotechnologically modified malt extract, such an extract being in particular sold by the applicant under the name Basaline™;

an agent for stimulating hyaluronane synthase 2 (HAS2) expression and/or activity, such as the plant extracts described in patent application FR 2 893 252 and in particular an aqueous extract of *galanga* (*Alpinia galanga*);

an agent for stimulating lysyl oxydase-like (LOXL) synthesis, such as a *Geophila cordifolia* extract and those described in patent application FR2855968, and in particular a dill extract;

an agent for stimulating intracellular ATP synthesis, in particular an extract of the *Laminaria digitata* alga;

an active agent for stimulating glycosaminoglycan synthesis, such as the product of milk fermentation;

an active agent which inhibits metalloproteinases (MMP), such as more particularly MMPs 1, 2, 3 and 9, such as retinoids and derivatives, oligopeptides and lipopeptides, lipoamino acids, the malt extract sold by BASF Beauty Care Solutions France under the tradename Collalift™, the hydrolysed extract of potato sold under the name Extracellium™ by BASF Beauty Care Solutions France SAS; lycopene; isoflavones, quercetin, kaempferol or apigenin.

They may also be agents for stimulating keratinocyte proliferation, in particular retinoids such as retinol and esters thereof, including retinyl palmitate, and phloroglucinol, and/or agents for stimulating keratinocyte differentiation, comprising for example minerals such as calcium and lignans such as secoisolariciresinol, and also the *Achillea millefolium* extract sold under the name Neurobiox™ by BASF Beauty Care Solutions France.

The tensioning agents that can be used in the invention can also be chosen from synthetic polymers, such as polyurethane latexes or acrylic latexes, polymers of natural origin, in particular polyholosides in the form of starch or in the form of carrageenans, alginates, agars, gellans, cellulose-based polymers and pectins, soya plant proteins and protein hydrolysates, mixed silicates, wax microparticles, colloidal particles of inorganic filler, chosen for example from silica, and silica-alumina composites; and also mixtures thereof. Finally, they may be cosmetic and/or dermatological ingredients, for example antimicrobial agents, free-radical scavengers, soothing agents, calmatives or relaxants, agents which act on the microcirculation in order to increase the radiance of the complexion, in particular of the face, and healing agents.

Among the antimicrobial agents that can be combined with the active ingredient of the invention in the present invention, mention may be made of 2,4,4'-trichloro-2'-hydroxydiphenyl ether (or triclosan), 3,4,4'-trichlorocarbanilide, phenoxyethanol, phenoxypropanol, phenoxyisopropanol, hexamidine isethionate, metronidazole and salts thereof, miconazole and salts thereof, itraconazole, terconazole, econazole, ketoconazole, saperconazole, fluconazole, clotrimazole, butoconazole, oxiconazole, sulfaconazole, sulconazole, terbinafine, undecylenic acid and salts thereof, benzoyl peroxide, 3-hydroxybenzoic acid, 4-hydroxybenzoic acid, phytic acid, N-acetyl-L-cysteine acid, lipoic acid, azelaic acid and salts thereof, arachidonic acid, resorcinol, octoxyglycerin, octanoylglycine, caprylyl glycol, 10-hydroxy-2-decanoic acid, farnesol, phytosphingosines and mixtures thereof. The free-radical scavengers may be vitamin C and derivatives thereof, including ascorbyl glucoside, phenols and polyphenols, in particular tannins; epigallocatechin and natural extracts containing same, in particular green tea extracts, anthocyans, phenol acids, stilbenes, active agents which scavenge monocyclic or polycyclic aromatic compounds, tannins and indol derivatives and/or active agents which scavenge heavy metals, such as EDTA, free-radical scavenging active agents such as vitamin E and derivatives thereof, such as tocopheryl acetate, bioflavonoids, coenzyme Q10 or ubiquinone.

The cosmetic and/or nutraceutical composition of the present invention can also contain one or more free-radical scavengers and/or antioxidants, such as a *Rhodiola crenulata* root extract sold under the name Rhodiomax™ by the applicant.

As soothing agents which are part of the composition of the invention, use may be made of pentacyclic triterpenes, ursolic acid and salts thereof, oleanolic acid and salts thereof, betulinic acid and salts thereof, salicylic acid salts and in particular zinc salicylate, bisabolol, allantoin, unsaturated omega 3 oils, cortisone, hydrocortisone, indomethacin and betamethasone, anti-inflammatory active agents, and in particular those described in application FR2847267, in particular the *Pueraria lobata* root extract sold under the name Inhipase™ by the applicant, and *Theobroma cacao* extracts. The vasoprotector or vasodilator active ingredients which act on the microcirculation can be chosen from flavonoids, ruscogenins, nicotinates and essential oils.

Finally, the composition can also contain, in combination with the extract according to the invention and/or gallic acid and/or one of the gallic acid derivatives, in particular vescalagin and/or castalagin, more preferentially castalagin, and/or the active ingredients mentioned above, draining and/or slimming ingredients and/or ingredients which prevent and/or treat the unaesthetic manifestations of cellulite, for example the orange peel appearance, such as caffeine and/or theophylline, *Theobroma cacao* polyphenols, a red alga hydrolysate sold under the name SlimExcess™ by the applicant, a *Coleus forskohlii* root extract, a *Ginkgo biloba* extract, particularly a *Ginkgo biloba* leaf extract, a *Cecropia obtusa* bark extract, a sea lettuce (*Ulva lactuca*) extract, a *Peumus boldus* leaf extract, an extract of *Smallanthus sonchifolius* also called yacon, or else a combination of hydrolysed extracts of *Coriandrum sativum* fruit and of *Citrus aurantium dulcis* fruit, a combination of hydrolysed extracts of *Celosia cristata* and of *Prunella vulgaris*, optionally combined with vasoprotector or vasodilator active ingredients which act on the microcirculation, chosen from escin, flavonoids, ruscogenins, nicotinates, essential oils, or a cosmetic active agent which stimulates the microcirculation of the skin in particular by means of a cold effect, such as mint extracts and menthol.

In addition, a subject of the present invention is a cosmetic care process comprising the application, preferentially topical application, to at least one area of skin and/or of mucous membrane, of the *Lythrum salicaria* extract according to the invention and/or of gallic acid and/or of one of the gallic acid derivatives, in particular vescalagin and/or castalagin, more preferentially castalagin, or of a cosmetic composition comprising such an extract according to the invention and/or gallic acid and/or one of the gallic acid derivatives, in particular vescalagin and/or castalagin, more preferentially castalagin, for maintaining and/or increasing collagen expression for maintaining and/or increasing the firmness of the skin and/or of the mucous membranes, in particular human skin and/or mucous membranes, and/or for maintaining and/or increasing lipolysis in skin adipocytes for inducing a slimming effect onto the skin and/or decreasing, preventing and/or treating the unaesthetic manifestations of cellulite, for example the orange peel appearance of the skin and/or the jodhpur thigh appearance. Preferentially, the collagen is type I collagen.

Advantageously, the cosmetic care process comprises the application, preferentially topical application, to at least one area of skin and/or of mucous membrane, of the *Lythrum salicaria* extract comprising at least 0.25%, preferentially at least 0.5%, more preferentially at least 1% by weight of vescalagin and/or of castalagin relative to the total weight of the *Lythrum salicaria* extract. In one embodiment of the invention, the cosmetic care process comprises the topical application, advantageously by massaging with circular movements, of the *Lythrum salicaria* extract according to the invention and/or of gallic acid and/or of one of the gallic acid derivatives, in particular of vescalagin and/or of castalagin, in the form of the cosmetic composition according to the invention.

According to one embodiment of the invention, the cosmetic care process is applied to at least one area of skin and/or of mucous membrane chosen from the stomach, the arms, the forearms, the knees, the bust, the thighs, the hips, the buttocks, the neck, the waist and/or the face, and preferentially the body, in particular to an area of skin comprising cellulite and/or the unaesthetic manifestations thereof, such as the orange peel appearance or the jodhpur thigh appearance, and/or to an area of skin which lacks firmness owning to non-pathological physiological variations, such as a change in diet, hormonal variations, in particular during puberty, pregnancy or menopause, but also a poor diet or a sedentary lifestyle, and more particularly in women.

A subject of the invention is also the extract of the *Lythrum salicaria* plant, preferentially obtained by aqueous extraction and more preferentially by extraction with an aqueous solution containing only water or containing at least 70% by weight of water relative to the total weight of the aqueous solution, advantageously obtained by extraction with an aqueous solution containing 25% by weight of alcohol, in particular of ethanol, relative to the total weight of the aqueous solution, and/or gallic acid and/or one of the gallic acid derivatives, in particular vescalagin and/or castalagin, more preferentially castalagin, alone or in a dermatological composition comprising it with a dermatologically acceptable excipient, for use thereof, advantageously topically, for the treatment and/or prevention of pathological conditions of the skin and/or of the mucous membranes involving a loss of expression of collagen, preferentially of type I collagen, more preferentially human type I collagen, and/or a pathological loss of firmness, such as telangiectasia, and/or involving a dysfunction in lipolysis in the adipose tissues, involved in particular in diseases such as obesity. Advantageously, the *Lythrum salicaria* extract is an extract of the aerial parts of the plant, that is to say a mixture of leaves, flowers, flower peduncles, and stem of the *Lythrum salicaria* plant. More advantageously, the *Lythrum salicaria* extract comprises at least 0.25%, preferentially at least 0.5%, more preferentially at least 1% by weight of gallic acid and/or of one of the gallic acid derivatives, in particular vescalagin and/or castalagin, relative to the total weight of the extract, in particular purified.

A subject of the invention is also the extract of the *Lythrum salicaria* plant, preferentially obtained by aqueous extraction and more preferentially by extraction with an aqueous solution containing only water or containing at least 70% by weight of water relative to the total weight of the aqueous solution, advantageously obtained by extraction with aqueous solution containing 25% by weight of alcohol, in particular of ethanol, and/or gallic acid and/or one of the gallic acid derivatives, in particular vescalagin and/or castalagin, alone or in a dermatological composition comprising it with a dermatologically acceptable excipient, for use thereof, advantageously topically, for the treatment and/or prevention of pathological conditions of the skin and/or of the mucous membranes involving a decrease in lipolysis and/or cellulite.

Examples referring to the description of the invention are present hereinafter. These examples are given by way of illustration and could not in any way limit the scope of the invention. Each of the examples has a general scope. The examples form an integral part of the present invention and any feature appearing to be novel over any prior art on the basis of the description taken as a whole, including the examples, forms an integral part of the invention.

EXAMPLE 1

Various Embodiments of the Invention For Obtaining a *Lythrum Salicaria* Extract According to the Invention a) Obtaining an extract of the aerial parts of *Lythrum salicaria* according to the Invention Five percent of aerial parts, that is to say a mixture of leaves, flowers, flower peduncles and stem, by weight of dry matter relative to the total weight of the mixture consisting of water and of the aerial parts of the *Lythrum salicaria* plant (w/w), were macerated in water, the water being in this case the sole solvent, for a period of 2 hours at ambient temperature, that is to say at 20° C. After maceration, the crude extract obtained was centrifuged for 10 min (8000 rpm) and then the supernatant was recovered and filtered (cut-off threshold of 0.45 µm). The extract of aerial parts at 5% (w/w) was then tested with regard to the increase in type I collagen protein expression under the conditions presented in the example 2 hereinafter.

b) Obtaining an Extract of the Aerial Parts of *Lythrum salicaria* According to the Invention Five percent of aerial parts, that is to say of a mixture of leaves, flowers, flower peduncles and stem, by weight of dry matter relative to the total weight of the mixture consisting of water and of the aerial parts of the *Lythrum salicaria* plant (w/w), were macerated in water at a temperature of 80° C. for a period of 1 hour. The crude extract was then centrifuged for 10 min (8000 rpm) and then the supernatant was filtered (0.45 µm).

c) Obtaining an Extract of the Aerial Parts of *Lythrum salicaria* According to the Invention Five percent of aerial parts, that is to say of a mixture of leaves, flowers, flower peduncles and stem, by weight of dry matter relative to the total weight of the mixture consisting of water and of the aerial parts of the *Lythrum salicaria* plant (w/w), were macerated at a temperature of 4° C., for a period of 16 hours, in water. The crude extract was then centrifuged for 10 min (8000 rpm) and then the supernatant was filtered (0.45 µm).

d) Obtaining an Extract of the Aerial Parts of *Lythrum salicaria* According to the Invention One percent of aerial parts by weight of dry matter relative to the total weight of the mixture consisting of water and of the aerial parts of the *Lythrum salicaria* plant (w/w) were macerated at a temperature of 4° C. for a period of 16 hours in water. The crude extract was then centrifuged for 10 min (8000 rpm) and then the supernatant was filtered (0.45 µm).

e) Obtaining an Extract of *Lythrum salicaria* Leaves According to the Invention Five percent of leaves by weight of dry matter relative to the total weight of the mixture consisting of the solvent and of the leaves (w/w) of the *Lythrum salicaria* plant were macerated in water as sole solvent for a period of 1 hour at a temperature of 80° C. The crude extract was then centrifuged for 10 min (8000 rpm) and then the supernatant was filtered (0.45 µm).

f) Obtaining an Extract of *Lythrum salicaria* Leaves According to the Invention An amount of 5% of *Lythrum salicaria* leaves by weight of dry matter relative to the total weight of the mixture consisting of water and of the *Lythrum salicaria* plant was macerated at ambient temperature, in this case 20° C., for a period of 2 hours, in a water/butylene glycol mixture (75/25; w/w). The crude extract was then centrifuged for 10 min (8000 rpm) in order to remove the insoluble fraction and then the supernatant was filtered (0.45 µm).

q) Obtaining a *Lythrum salicaria* Extract Comprising Vescalagin and/or Castalagin According to the Invention An amount of 10% of the aerial parts, that is to say of the mixture of leaves, flowers, flower peduncles and stem of *Lythrum salicaria*, by weight of dry matter relative to the total weight of the mixture consisting of the solvent and of the aerial parts of the plant, was macerated with stirring at ambient temperature, in this case 20° C., for a period of 24 hours, in a water/ethanol mixture (75/25; w/w).

The extract was then purified in a first step by solid phase extraction (SPE) on a C18-grafted silica solid phase. The extract was deposited in aqueous-alcoholic solution containing 20% of methanol and 0.5% of formic acid. The elution was carried out with this same solvent. The extract obtained was thus concentrated by evaporation and then lyophilized. The extract obtained was then purified in a second step by semi-preparative high performance liquid chromatography (HPLC) on a Synergi Fusion (Phenomenex) column having the dimensions 250×10 mm. The elution was carried out with the gradient of 0.5% formic acid and methanol.

The purified extract thus obtained comprises vescalagin and/or castalagin, in a total amount of molecules of 1% by weight relative to the total weight of the purified extract.

Maltodextrin was added to the extract and then the extract was concentrated by evaporation and then lyophilized.

EXAMPLE 2

Demonstration of the Effect of a *Lythrum Salicaria* Extract According to the Invention on Type I Collagen Protein Expression Protocol:

The experimental conditions for demonstrating the increase in type I collagen protein expression are those set out in example 1 of the international application published under number WO 2012/175454.

Normal, that is to say non-pathological, human fibroblasts obtained from abdominal biopsies from a healthy donor were seeded into 96-well plates and cultured in a defined medium (FGM) up to 100% confluence, which is obtained after 3 days of culture.

The *Lythrum salicaria* extract according to the invention, prepared according to example 1 a of the present invention, was added at a final concentration of 1% (w/w) to the culture medium. The same culture medium without the addition of extract according to the invention was used as a control (non-treated control).

After 48 hours of culture post-confluence at 37° C., the culture medium was removed and eliminated. A cell lysis step was carried out and the lysate was then removed and analysed. A DNA assay was carried out on the lysates so as to express the collagen protein expression per cell.

The double-stranded DNA was assayed by the bisbenzimide method (Invitrogen, Quant-iT™ PicoGreen® dsDNA). The DNA concentration is proportional to the number of viable cells and makes it possible to rationalize the fluorescence read with respect to a number of cells.

The type I collagen was assayed by means of the immunochemical technique as follows:

An anti-type I collagen antibody was incubated for 30 minutes with the cell lysate. After rinsing with PBS, the europium-coupled secondary antibody (Perkin Elmer) was added. A revealing solution was added and the fluorescence was measured using an EnVision multiplate reader (Perkin Elmer).

For each condition, the time-resolved fluorescence (TRF) was measured in each well and rationalized with respect to the amount of DNA assayed in the well. The (fluorescence/DNA concentration) ratio was calculated.

For each condition, the results are expressed by the percentage of the mean of the protein expressions relative to the protein expressions measured in the control (non-treated control) (n=6).

Results:

|  | Mean | Standard deviation |
|---|---|---|
| Control | 100 | 1 |
| 1% (w/w) Lythrum salicaria extract 1a) | 196.6 | 14.5 |

CONCLUSION

The *Lythrum salicaria* extract according to the invention induced an increase in the type I collagen protein expression in human fibroblasts cultured in vitro. The extract according to the invention can thus be used for increasing the firmness of the skin and/or the mucous membranes.

EXAMPLE 3

Effect of Various *Lythrum Salicaria* Extracts According to the Invention on the Increase in Lipolysis of Skin Adipocytes Example 3a

*Lythrum Salicaria* Extract According to Example 1a)

Protocol:

Adipocytes were obtained by differentiation of human preadipocytes as follows: normal, that is to say non-pathological, non-cancerous, human preadipocytes were inoculated into a growth medium enriched with growth factors (PAGS 7252 Cliniscience) and foetal calf serum (FBS). After 3 days of culture, the culture medium was replaced with a differentiation medium (PADM 7221 Cliniscience) containing the growth factors and the FBS. After 2 days of culture, the differentiation medium was replaced with a standard medium containing 1% of FBS. The adipocytes formed were then incubated for a period of 16 hours in the presence of the *Lythrum salicaria* extract according to example 1a) at a final concentration of 1% by weight relative to the total weight of the final culture medium and of the extract.

The lipolysis was evaluated by quantification of the glycerol released into the culture medium. The quantification of the glycerol was obtained by means of an enzymatic method (Libios K-GCROL kit) and measurement of the optical density at 340 nm. The results are expressed as percentage relative to the control (culture medium without *L. salicaria* extract) (Base 100). The results presented are the mean of 3 assays (n=3).

Results:

|  | Mean | Standard deviation |
|---|---|---|
| Control | 100 | 20.2 |
| 1% (w/w) Lythrum salicaria extract 1a) | 210.3 | 31.8 |

CONCLUSION

The results show an increase in lipolysis in the adipocytes cultured in the presence of the *Lythrum salicaria* extract, showing the capacity of the extract to induce a slimming effect and to decrease the unaesthetic manifestations of cellulite, for example the orange peel appearance and/or the jodhpur thigh appearance.

Example 3b

*Lythrum salicaria* Extract Comprising Vescalagin and Castalagin According to Example 1g)

Protocol:

Adipocytes were obtained by differentiation of 3T3-L1 murine preadipocytes as follows: the murine preadipocytes were inoculated into a growth medium enriched with neonatal calf serum. After 3 days of culture, the culture medium was replaced with a differentiation medium containing the differentiation factors Iso-Butyl-Methyl-Xanthine (IBMX) and Dexamethasone, and foetal calf serum (FCS). After 2 days of culture, the differentiation medium was replaced with a standard medium containing 10% of FCS and incubated for 8 days. The adipocytes formed were then incubated for a period of 16 hours in the presence of the *Lythrum salicaria* extract according to example 1g) at a final concentration of $2.5 \times 10^{-3}\%$ by weight relative to the total weight of the final culture medium and of the extract.

The lipolysis was evaluated by quantification of the glycerol released into the culture medium. The quantification of the glycerol was obtained by means of an enzymatic method (Libios K-GCROL kit) and measurement of the optical density at 340 nm.

The results are expressed as percentage relative to the control (culture medium without *L. salicaria* extract) (Base 100). The results presented are the mean of an assay carried out in "quadruplet" (n=4).

Results:

|  | Mean | Standard deviation |
|---|---|---|
| Control | 100 | 12 |
| $2.5 \times 10^{-3}\%$ (w/w) Lythrum salicaria extract 1g) | 151 | 4 |

CONCLUSION

The results showed an increase of at least 35% in lipolysis in the murine adipocytes cultured in the presence of the *Lythrum salicaria* extract comprising vescalagin and castalagin, showing the capacity of the extract to induce a slimming effect and to decrease the unaesthetic manifestations of cellulite, for example the orange peel appearance and/or the jodhpur thigh appearance.

EXAMPLE 4

Example of Cosmetic and/or Dermatological Ingredients Containing the *Lythrum Salicaria* Extract According the Invention The methods known to those skilled in the art were carried out in order to mix together the various ingredients according to the present invention. The percentages expressed are percentages by weight relative to the total weight of the composition.

a) The *Lythrum salicaria* Extract According to the Invention is the One Obtained According to Example 1a

| | |
|---|---|
| *Lythrum salicaria* extract (Ex. 1a)) | 5% |
| Hexylene glycol | 0.5% |
| Caprylyl glycol | 1% |
| Xanthan gum | 0.5% |
| Water | qs 100 | b) The *Lythrum salicaria* Extract According to the Invention is the One Obtained According to Example 1b

| | |
|---|---|
| *Lythrum salicaria* extract (Ex. 1b)) | 5% |
| Hexylene glycol | 0.5% |
| Caprylyl glycol | 1% |
| Xanthan gum | 0.5% |
| Water | qs 100 | c) The *Lythrum salicaria* Extract According to the Invention is the One Obtained According to Example 1c

| | |
|---|---|
| *Lythrum salicaria* extract (Ex. 1 g)) | 1-5% |
| Maltodextrin | 80% |
| Water | qs 100 |

EXAMPLE 5

Example of Cosmetic Compositions Containing the Extract According to the Invention The compositions hereinafter are prepared according to methods known to those skilled in the art, in particular as regards the various phases to be mixed together.

5a) Cosmetic Composition Containing a *Lythrum salicaria* Extract According to the Invention

| | |
|---|---|
| Cosmetic ingredient* | 3.00 |
| EDTA | 0.05 |
| Steareth-2 | 2.00 |
| Steareth-21 | 2.50 |
| Cetearyl alcohol | 1.00 |
| Propylheptyl caprylate | 15.00 |
| Sodium hydroxide (30% in solution) | 0.10 |
| Mixture of phenoxyethanol, chlorphenesin, benzoic acid, butylene glycol, sorbic acid (Germazide ™ PBS) | 1.25 |
| Mixture of polyacrylate-X, isohexadecane and polysorbate 60 (Sepigel ™ SMS 60) | 4.00 |
| Water | qs 100 |

*The cosmetic ingredient is prepared according to example 4a or 4c above. The amounts indicated are in percentage by weight relative to the total weight of the composition.

5b) Cosmetic Composition Comprising a *Lythrum salicaria* Extract According to the Invention

| | |
|---|---|
| Cosmetic ingredient* | 3.00 |
| EDTA | 0.05 |
| Steareth-2 | 2.00 |
| Steareth-21 | 2.50 |
| Cetearyl alcohol | 1.00 |
| Propylheptyl caprylate | 15.00 |
| Sodium hydroxide (30% in solution) | 0.10 |
| Mixture of phenoxyethanol, chlorphenesin, benzoic acid, butylene glycol, sorbic acid (Germazide ™ PBS) | 1.25 |
| Mixture of polyacrylate-X, isohexadecane and polysorbate 60 (Sepigel ™ SMS 60) | 4.00 |
| Water | qs 100 |

*The cosmetic ingredient is in this case prepared according to example 4b or 4c above. The amounts indicated are in percentage by weight relative to the total weight of the composition.

EXAMPLE 6

Example of a Dermatological Composition in Ointment Form Containing the Extract According to the Invention The composition hereinafter is prepared according to methods known to those skilled in the art, in particular as regards the various phases to be mixed together.

The amounts indicated are in percentage by weight relative to the total weight of the composition.

| | |
|---|---|
| Ingredient* | 3.00 |
| Excipient: | |
| Low-density polyethylene | 5.50 |
| Liquid paraffin | qs 100 |

*The ingredient is prepared according to example 4b or 4c above. The ingredient according to the invention is in this case sterilized and then dried before being incorporated into the composition in ointment form.

The invention claimed is:

1. A cosmetic method for inducing a slimming effect onto the skin and/or decreasing, preventing and/or treating unaesthetic manifestations of cellulite, said method comprising administering to a human being whose skin is in need thereof an effective amount of a *Lythrum salicaria* extract and/or one of the gallic acid derivatives selected from the group consisting of vescalagin, castalagin and mixture thereof,
   wherein the administration consists of the topical application to at least one area of healthy skin in need thereof.

2. The method of claim 1, wherein the *Lythrum salicaria* extract and/or one of the gallic acid derivatives selected from the group consisting of vescalagin, castalagin and mixture thereof maintains and/or increases collagen expression in the skin.

3. The method of claim 2, wherein the collagen is type I collagen.

4. The method of claim 1, wherein the *Lythrum salicaria* extract and/or one of the gallic acid derivatives selected from the group consisting of vescalagin, castalagin and mixture thereof maintains and/or increases lipolysis in skin adipocytes.

5. The method according to claim 4, wherein the at least one area the skin in need thereof is an area of skin comprising cellulite and/or unaesthetic manifestations thereof.

6. The method of claim 5, wherein the at least one area the skin in need thereof is an area of skin comprising the orange peel appearance or the jodhpur thigh appearance.

7. The method of claim 1, wherein the *Lythrum salicaria* extract is an extract obtained by aqueous extraction.

8. The method of claim 1, wherein the *Lythrum salicaria* extract is an extract of aerial parts of the plant.

9. The method of claim 1, wherein the *Lythrum salicaria* extract is obtained by extraction of an amount of from 0.1% to 10% by weight of dry matter of at least one part of the *Lythrum salicaria* plant relative to the total weight of the solvent/plant mixture (w/w).

10. The method of claim 1, wherein the *Lythrum salicaria* extract and/or one of the gallic acid derivatives is selected from the group consisting of vescalagin, castalagin and mixture thereof is solubilized in an aqueous solution comprising hexylene glycol and caprylyl glycol or a mixture thereof.

11. The method of claim 1, wherein the *Lythrum salicaria* extract comprises at least 0.25% by weight of vescalagin and/or castalagin relative to the total weight of the extract.

12. The method of claim 1, wherein the *Lythrum salicaria* extract comprises at least 20% by weight of maltodextrin relative to the total weight of the extract and the maltodextrin.

13. The method of claim 1, wherein the *Lythrum salicaria* extract and/or one of the gallic acid derivatives selected from the group consisting of vescalagin, castalagin and mixture thereof is present in a cosmetic composition comprising at least one cosmetically acceptable excipient.

14. The method of claim 13, wherein the *Lythrum salicaria* extract is present in the composition at a concentration of from $1\times10^{-4}$% to 10% by weight relative to the total weight of the composition.

15. The method of claim 13, wherein one of the gallic acid derivatives selected from the group consisting of vescalagin, castalagin and mixture thereof is present in the composition at a total final concentration of the selected gallic acid derivative of from $2.5\times10^{-7}$ to 0.1% relative to the total weight of the composition.

16. The method of claim 13, wherein the cosmetic composition is in form of an aqueous or oily solution, a cream or a gel which is aqueous or an oily gel, a shampoo, a milk, an emulsion, a microemulsion or a nanoemulsion, a mask, a serum, a lotion, a liquid soap, a dermatological bar, an ointment, a foam, or a patch.

17. The method of claim 1, wherein the area of skin and/or mucous membrane is chosen from one or more of the stomach, the arms, the forearms, the knees, the bust, the thighs, the hips, the buttocks, the neck, the waist or the face.

18. The method according to claim 17, wherein the area of skin is chosen from one or more of the stomach, the arms, the thighs, the buttocks, the waist or the hips.

19. The method according to claim 18, wherein the area of skin is chosen from one of more of the thighs or the hips.

20. The method of claim 1, wherein the at least one area the skin in need thereof is an area of skin comprising cellulite and/or unaesthetic manifestations thereof.

21. The method of claim 20, wherein the at least one area the skin in need thereof is an area of skin comprising the orange peel appearance or the jodhpur thigh appearance.

* * * * *